(12) United States Patent
Le

(10) Patent No.: US 10,596,292 B2
(45) Date of Patent: Mar. 24, 2020

(54) COMPACT AROMATIC DIFFUSER AND METHOD OF USE

(71) Applicant: Son Le, Orem, UT (US)

(72) Inventor: Son Le, Orem, UT (US)

( * ) Notice: Subject to any disclaimer, the term of this patent is extended or adjusted under 35 U.S.C. 154(b) by 115 days.

(21) Appl. No.: 15/845,808

(22) Filed: Dec. 18, 2017

(65) Prior Publication Data

US 2019/0184051 A1 Jun. 20, 2019

(51) Int. Cl.
| | | |
|---|---|---|
| *A61L 9/12* | (2006.01) | |
| *A61L 9/14* | (2006.01) | |
| *A62B 18/02* | (2006.01) | |
| *A61M 11/00* | (2006.01) | |
| *A62B 7/00* | (2006.01) | |
| *A61M 16/06* | (2006.01) | |

(52) U.S. Cl.
CPC .............. *A61L 9/122* (2013.01); *A61L 9/125* (2013.01); *A61L 9/127* (2013.01); *A61L 9/14* (2013.01); *A61L 2209/11* (2013.01); *A61L 2209/13* (2013.01); *A61L 2209/133* (2013.01); *A61L 2209/15* (2013.01); *A61M 11/00* (2013.01); *A61M 16/06* (2013.01); *A62B 7/00* (2013.01); *A62B 18/02* (2013.01)

(58) Field of Classification Search
CPC .................................. A61L 9/12; A61L 9/122
See application file for complete search history.

(56) References Cited

U.S. PATENT DOCUMENTS

| | | | | |
|---|---|---|---|---|
| 4,356,969 A | * | 11/1982 | Obermayer | A01M 1/2044 239/56 |
| 5,377,363 A | * | 1/1995 | Shieh | A61L 9/12 4/222 |
| 9,089,621 B1 | * | 7/2015 | Leyva | B01F 3/04 |
| 2005/0066976 A1 | * | 3/2005 | Wondka | A61M 16/06 128/207.18 |
| 2010/0022819 A1 | * | 1/2010 | Randall | A61M 11/041 600/27 |
| 2012/0055480 A1 | * | 3/2012 | Wilkinson | A61M 16/024 128/205.11 |
| 2013/0228181 A1 | * | 9/2013 | Ahmad | A61M 16/0069 128/204.23 |

\* cited by examiner

*Primary Examiner* — Donald R Spamer
(74) *Attorney, Agent, or Firm* — Workman Nydegger

(57) ABSTRACT

A compact aromatic diffuser configured to be used in conjunction with a breathing mask, allowing full consumption of the diffused essential oil by the user. The compact aromatic diffuser may also be used as a hand held inhaler for application proximate the user's face or a standalone diffuser for treating the atmosphere in a room or closed compartment.

20 Claims, 6 Drawing Sheets

COMPACT AROMATIC DIFFUSER AND METHOD OF USE

BACKGROUND

Aromatic diffusers are ubiquitous fixtures in homes and offices used to primarily to mask odors in the atmosphere. However, many proponents of essential oil usage tout the benefits of the essential oils beyond the aromatic quality and argue that the oils have properties that clean the air, killing bacteria and viruses, reduce the effects of a sickness, relieve stress, promote sleep, and numerous other positive attributes.

Typical diffusers are counter-top models that are configured to diffuse the essential aroma into the entire room. The counter-top models require access to an electrical supply and are not convenient to move around. The diffused essential oil is disseminated throughout the atmosphere and is not focused for the use or therapeutic needs of an individual person.

What is needed is a diffuser having a compact configuration for easy portability and the ability to distribute therapeutic essential oil aroma directly to an individual user.

SUMMARY OF THE INVENTION

The disclosure of the present invention relates to a compact aromatic diffuser or more specifically to a compact aromatic diffuser configured for portability, and most importantly, configured for ease of use by an individual user. The compact aromatic diffuser can be conveniently used as a lightweight portable diffuser that is placed close to a user, may be held by the user proximate the mouth and nose allowing the user to readily inhale the aromatic essential oil, or the diffuser is configured to be used in conjunction with a conventional breathing mask allowing the user to consume the entire diffused airstream and allowing for hands free use.

One embodiment of the present invention or compact aromatic diffuser is comprised of a diffuser body portion configured to house a battery, programmable computer board (PCB) controller, a distribution fan and felt wicking element. The battery may be replaceable but it is contemplated that the battery is a permanent rechargeable. The PCB is configured to provide an on/off function, control the fan speed and may be configured to provide automated functions, such as, an automatic shut down in order to conserve the battery. The body portion having a plurality of intake holes just below the position of the fan. Airflow from the fan is directed over the felt wicking element and out through an exhaust opening. In one embodiment the exhaust opening is configured to be adapted to the intake of a breathing mask, such as the mask used in various medical procedures or a mask configured for use with a continuous positive airway pressure (CPAP) machine. In yet another embodiment the exhaust opening is configured to receive a plurality of adaptor fittings that are configured to fit different medical masks or masks having an intake opening of a different diameter or shape. The adaptor fitting may also be configured to have rounded edges in order to protect the user when the device is placed proximate the user's face.

In one embodiment of the present invention the user will place a few drops of the essential oil on the felt wicking element before turning on the diffuser. In another embodiment the felt wicking element is replaceable, and the user may choose to apply different essential oils or a combination of oils to a plurality of felts which may be interchanged into the diffuser body. The diffuser cavity inside of the diffuser body may include slots, braces or rails configured to hold the felt wicking element in place. A container having multiple compartments may be provided for storing a plurality of felt wicking elements.

Another embodiment of the present invention includes a multi-compartment diffuser cartridge configured to be fitted directly to the diffuser body or connected via an adaptor fitting. The multi-compartment diffuser cartridge configured to have two or more compartments, each compartment having the capacity to store a felt wicking element that is treated with a different essential oil. The cartridge is moveable allowing the user to position one of the compartments over the air exhaust from the compact diffuser, allowing the circulated air to flow over the felt wicking element in that compartment and exit through a vent system. The lid of the cartridge configured to create an air tight seal between corresponding compartments. In one embodiment there are two wicking element compartments, in another embodiment there are three wicking element compartments, in another embodiment there are four wicking element compartments, in another embodiment there are five wicking element compartments, and in yet another embodiment there are more than five wicking element compartments.

In one embodiment the diffuser body, the adaptor fittings, the multi-compartment diffuser cartridge and, possibly other components, are manufactured using a fluorinated plastic or a fluorinated plastic with glass fill formulated to resist degradation from exposure to the essential oil.

BRIEF DESCRIPTION OF DRAWINGS

The following description of the embodiments can be understood in light of the Figures which illustrate specific aspects of the embodiments and are part of the specification. Together with the following description, the Figures demonstrate and explain the principles of the embodiments. In the Figures the physical dimensions of the embodiment may be exaggerated for clarity. The same reference numerals or word descriptions in different drawings represent the same element, and thus their descriptions may be omitted.

Figure 1:
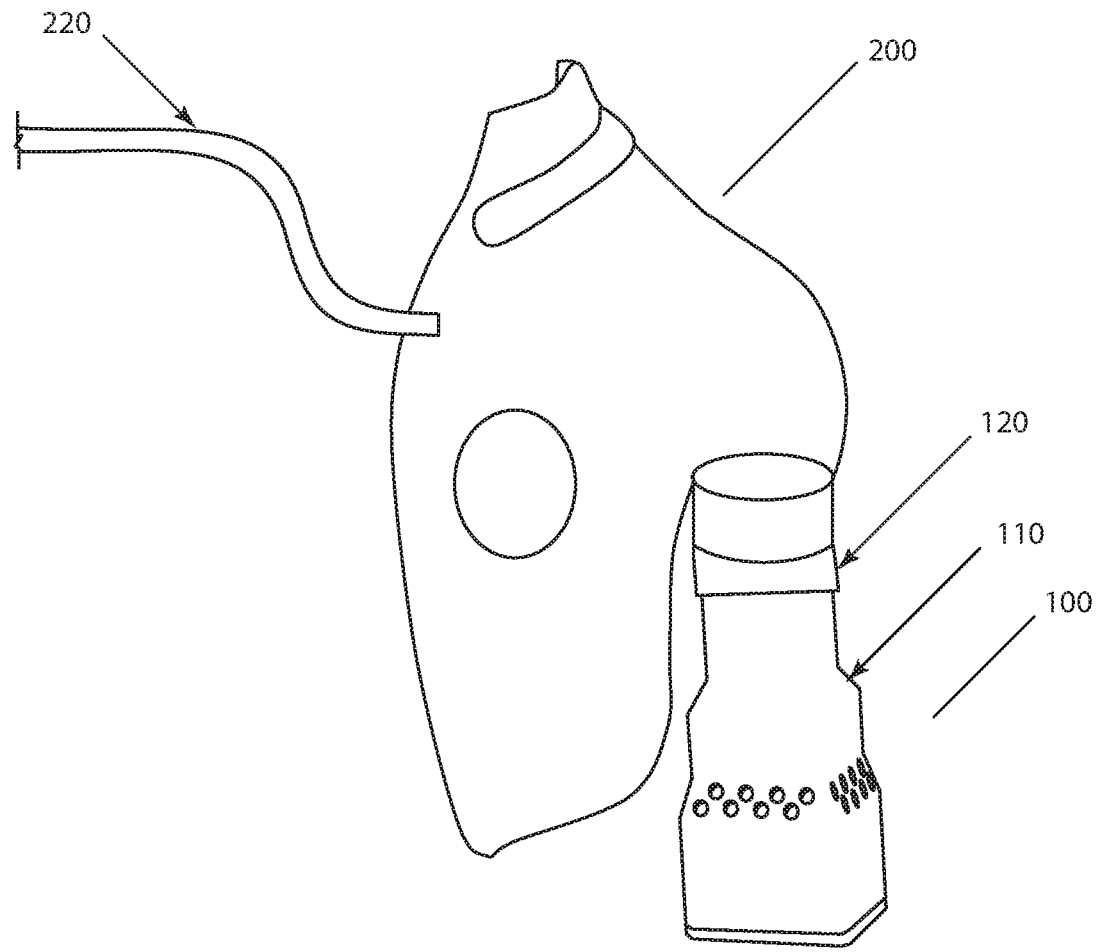
FIG. 1 is a perspective view of a compact aromatic diffuser used in conjunction with a breathing mask.

It is to be understood that the above mentioned arrangements are only illustrative of the application of the principles of the present disclosure. Numerous modifications or alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

DETAILED DESCRIPTION OF THE DRAWINGS

Figure 4:
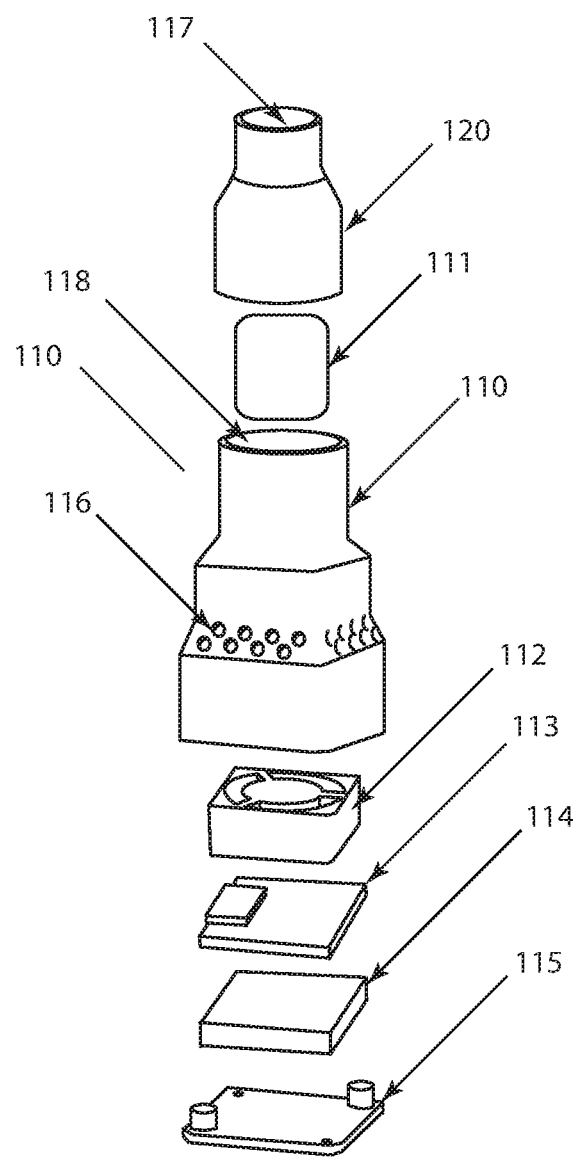
FIG. 4 is an exploded view of the compact aromatic diffuser.

A shown in FIG. 4 is a compact aromatic diffuser 100 having a body portion 110 configured to house a battery 114, PCB controller 113, distribution fan 112, aromatic wicking felt 111 and a base cover 115. A plurality of intake holes 116 allow air to pass through the body portion 110, through fan 112, through a diffuser cavity 118, over the wicking felt 111 and through an exhaust opening 117. In one embodiment the exhaust end of the body portion configured to receive one or more adaptor fittings 120. The adaptor fittings 120 may be configured to mate with the intake openings 210 of variety of the commercial breathing face masks 200 (see FIG. 1).

FIG. 1 depicts the compact aromatic diffuser 100 fitted to a breathing mask 200. The breathing mask 200 including a head strap 220 configured to secure the mask 200 to the user's face, over the mouth and nose. The body portion 110 including an adaptor fitting 120 allowing the compact aromatic diffuser 100 to securely attach to the breathing mask 200 at the mask intake opening 210.

Figure 2:
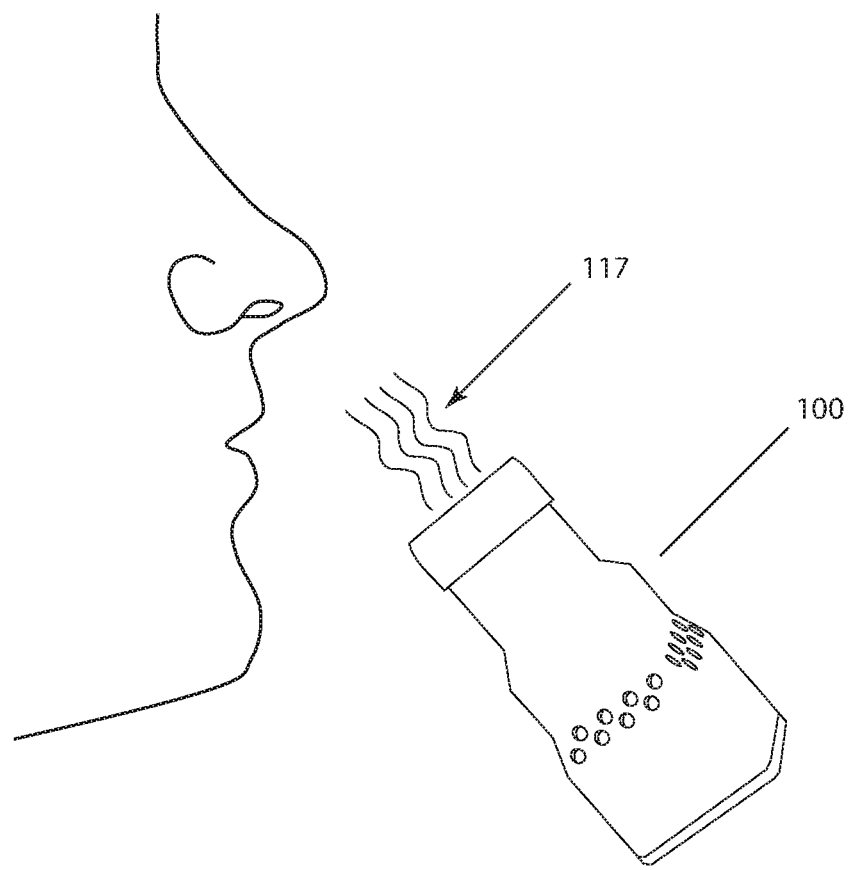
FIG. 2 is a perspective view of the compact aromatic diffuser in direct personal use.

FIG. 2 shows how a user can enjoy the compact aromatic diffuser 100 as an inhaler by directly discharging diffused essential oil vapor 117 proximate the user's nose and mouth.

Figure 3:
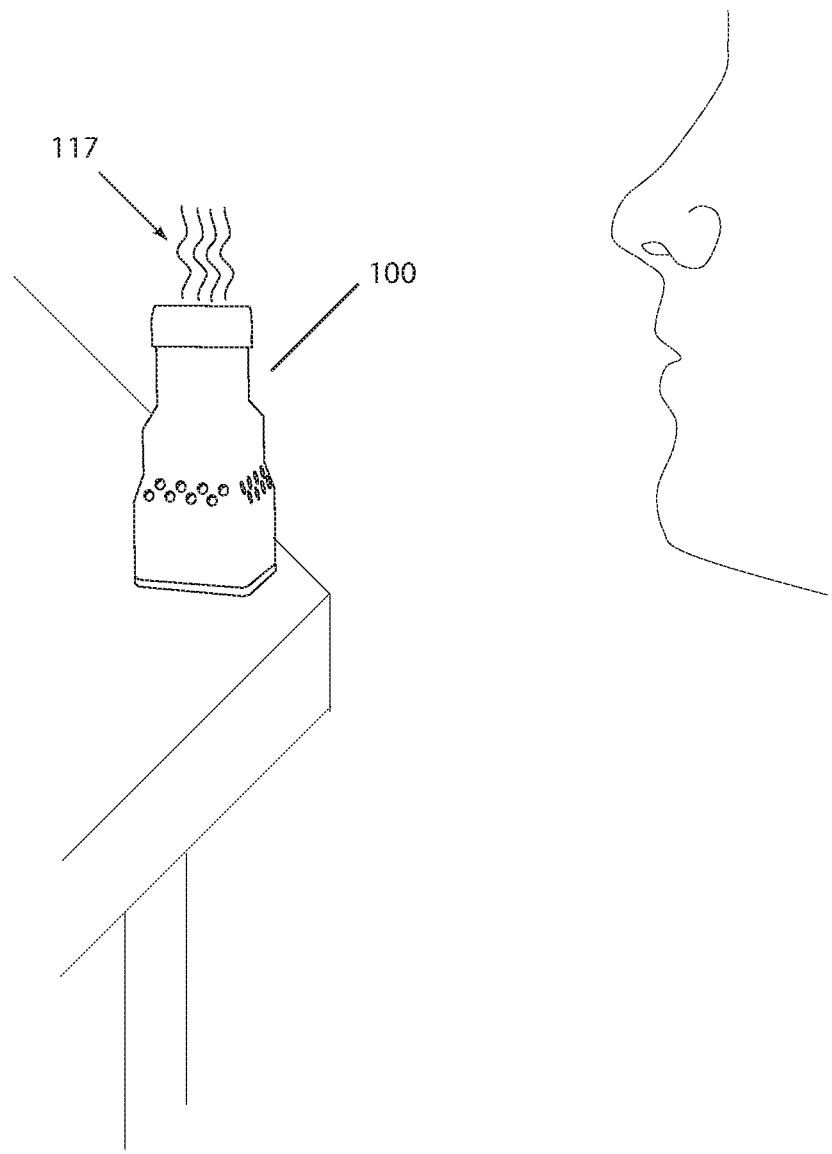
FIG. 3 is a perspective view of the compact aromatic diffuser for static use.

The compact aromatic diffuser 100 can be used to discharge vapor 117 directly into a home, office or automobile is depicted in FIG. 3.

Figures 5A, 5B:
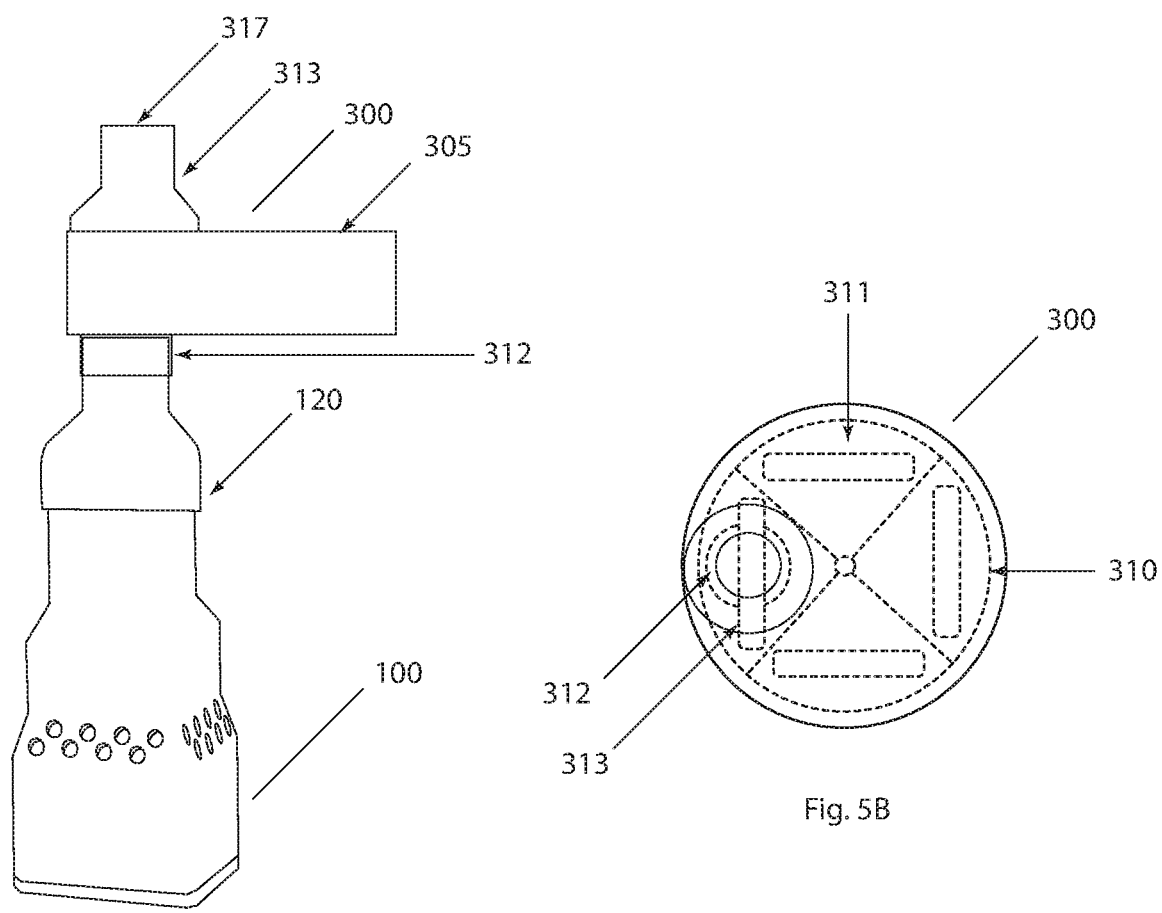
FIG. 5A is a perspective view of the compact aromatic diffuser with a multi-compartment diffuser cartridge installed.
FIG. 5B is a top view of the multi-compartment diffuser cartridge, and, FIG. 6 is a perspective view of a compact aromatic diffuser and diffuser cartridge used in conjunction with a breathing mask.

FIG. 5A is a perspective view of the compact aromatic diffuser 100 with a multi-compartment diffuser cartridge 300 installed. In one embodiment the cartridge 300 can installed on the diffuser body 100 using an adaptor fitting 120 configured to insert into an air inlet 312 on the bottom of the cartridge 300. As shown in FIG. 5B, cartridge 300 configured having a plurality of air tight compartments 310 having accommodations to fit a felt wicking element 311. Each felt wicking element 311 can be treated with a different essential oil and rotated over the air inlet 312 where the air flow will travel over the wicking element 311 and discharge through exhaust vent 317 of the top adaptor fitting 313 configured to engage with a breathing mask 200. The top adaptor fitting 313 formed in the top cover 305.

Figure 6:
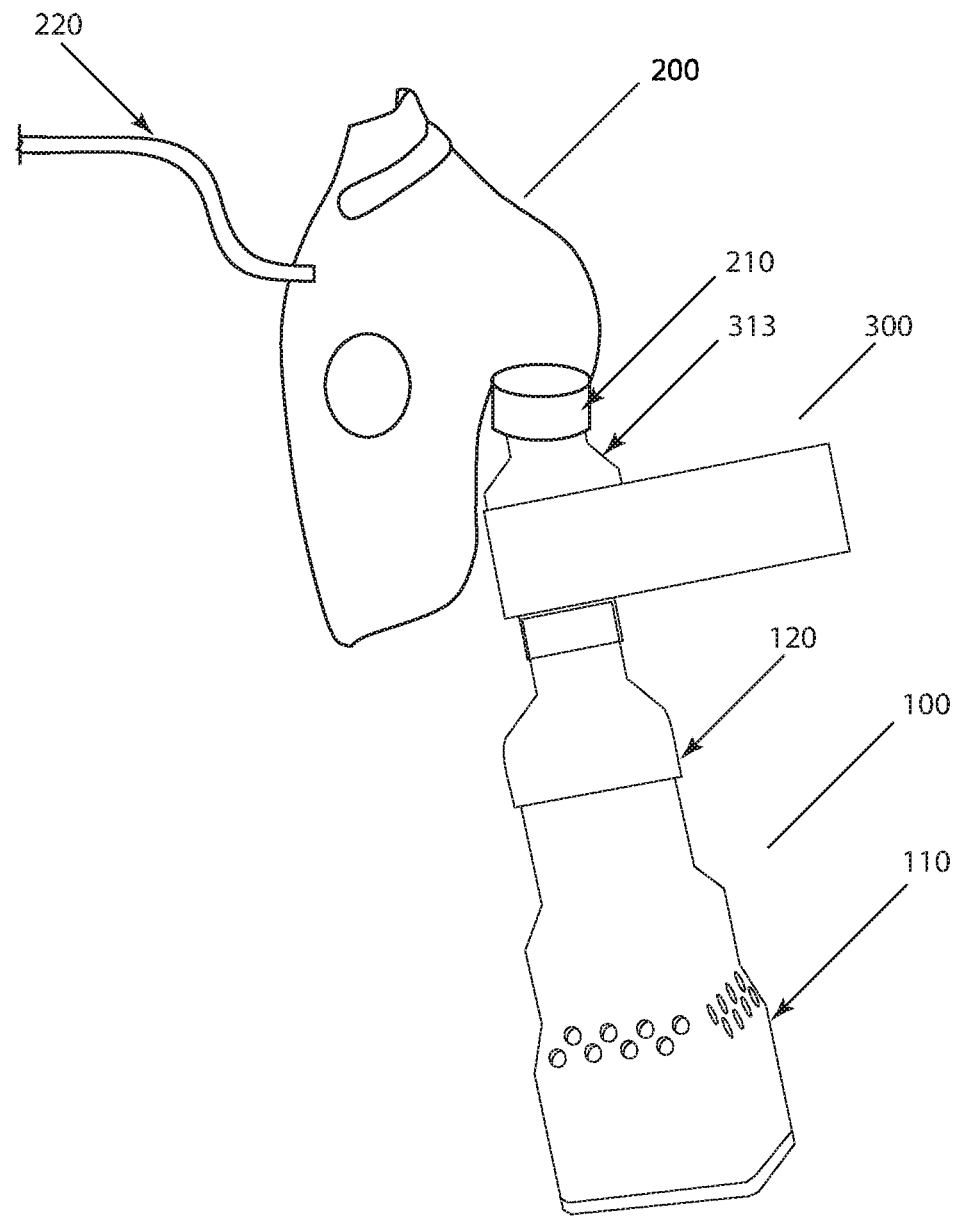

FIG. 6 is a perspective view of the compact diffuser 100, having a body potion 110 and adaptor fitting 120. The compact diffuser 100 having a multi-compartment diffuser cartridge 300 installed using the adaptor fitting 120. The diffuser cartridge 300 having a top adaptor fitting 313 configured to engage with the intake opening 210 of the breathing mask 200. When operating the diffuser 100 with the multi-compartment diffuser cartridge 300, the user may simple rotate the cartridge 300 in order to change the desired essential oil.

The invention claimed is:

1. A compact diffuser configured for portability and for distributing therapeutic essential oil aroma directly to an individual user, the compact diffuser comprising,
    a body portion, the body portion defining a diffuser cavity and including,
        a battery;
        a distribution fan powered by the battery, wherein the distribution fan is disposed within the diffuser cavity and proximate a plurality of holes formed in a sidewall of the body portion, wherein the distribution fan is configured to generate an airflow by drawing air through the plurality of holes and into the diffuser cavity during operation;
        a programmable computer board disposed within the diffuser cavity and operably connected to the distribution fan;
        an exhaust opening; and
        at least one felt wicking element associated with the diffuser cavity such that the airflow generated by the distribution fan is directed along the at least one felt wicking element and out of the diffuser cavity; and
    an adaptor fitting, wherein the adaptor fitting is configured to engage the exhaust opening of the compact diffuser and to couple the compact diffuser with an intake opening of a breathing mask.

2. The compact diffuser of claim 1, additionally including slots, braces, or rails disposed within the diffuser cavity that are configured to hold the at least one felt wicking element inside the diffuser cavity defined by the body portion.

3. The compact diffuser of claim 1, wherein the at least one felt wicking element is interchangeable.

4. The compact diffuser of claim 1, wherein the adaptor fitting is configured to insert into the intake opening of the breathing mask, the intake opening having a first diameter.

5. The compact diffuser of claim 1, wherein the adaptor fitting is configured to insert into the intake opening of the breathing mask, the intake opening having a second diameter.

6. The compact diffuser of claim 1, wherein the programmable computer board is configured with an automatic shutdown of the distribution fan to conserve power of the battery.

7. The compact diffuser of claim 1, including a multi-compartment diffuser cartridge configured to be fitted directly to the body portion or connected to the body portion via the adaptor fitting of the compact diffuser and to provide a plurality of interchangeable compartments that each have capacity to store a differently treated felt wicking element, the multi-compartment diffuser cartridge including:
    an intake opening configured to align with the exhaust opening of the body portion and extend the diffuser cavity therethrough; and
    a top adaptor fitting aligned with and positioned opposite from the intake opening;
    wherein the intake opening is configured to fit on the adaptor fitting of the compact diffuser,
    wherein the top adaptor fitting is configured to couple with the intake opening of the breathing mask, and
    wherein a first of the at least one felt wicking elements is disposed within a first compartment of the multi-compartment diffuser cartridge and aligned between the intake opening and the top adaptor fitting.

8. The compact diffuser of claim 7, wherein the body portion, the adaptor fitting of the compact diffuser, and the multi-compartment diffuser cartridge are made using a material formulated to resist degradation from exposure to essential oil.

9. The compact diffuser of claim 1, wherein the battery is a permanent, rechargeable battery.

10. The compact diffuser of claim 1, wherein the programmable computer board is configured to at least provide a variable speed control for the distribution fan.

11. The compact diffuser of claim 1, wherein distribution fan and exhaust opening are aligned along a longitudinal axis of the body portion.

12. The compact diffuser of claim 1, wherein the distribution fan and the exhaust opening are centrally aligned.

13. The compact diffuser of claim 7, wherein the distribution fan, the exhaust opening, the intake opening, and at least one compartment of the plurality of interchangeable compartments that store the differently treated felt wicking elements are centrally aligned.

14. The compact diffuser of claim 7, further including a second felt wicking element disposed within a second compartment of the multi-compartment diffuser cartridge, the multi-compartment diffuser cartridge being operable to change from the first compartment that houses the first felt wicking element to the second compartment that houses the second felt wicking element by rotating the multi-compartment diffuser cartridge.

15. The compact diffuser of claim 14, wherein the first compartment is separated from the second compartment by an airtight barrier.

16. The compact diffuser of claim 14, wherein the first and second felt wicking elements are differentially treated.

17. The compact diffuser of claim 7, wherein each of the plurality of interchangeable compartments are airtight compartments.

18. A method of using a compact diffuser comprising:
providing a breathing mask, the breathing mask having an intake opening;
providing the compact diffuser of claim 1;
applying essential oil to the at least one felt wicking element;
installing the at least one felt wicking element in the diffuser cavity;
installing the adaptor fitting over the exhaust opening of the body portion;
attaching the adaptor fitting to the intake opening of the breathing mask;
installing the breathing mask on the user; and
activating the distribution fan such that airflow created by the distribution fan is brought through the plurality of holes formed in the sidewall of the body portion, along the at least one felt wicking element, through the exhaust opening of the compact diffuser, and into the breathing mask via the intake opening, where essential oil vapor is discharged proximate the user's nose and mouth.

19. A personal and portable essential oil diffusing system, comprising:
a compact diffuser, including:
a body portion that defines a diffuser cavity;
a battery disposed within the diffuser cavity;
a distribution fan disposed within the diffuser cavity and powered by the battery;
a programmable computer board disposed within the diffuser cavity and operably connected to the distribution fan, the programmable computer board being configured to control one or more operations of the distribution fan; and
an exhaust opening formed by the body portion;
a multi-compartment diffuser cartridge configured to be directly fitted to the body portion and including:
a first compartment housing a first felt wicking element; and
a second compartment housing a second felt wicking element,
wherein the first compartment and second compartment are rotatably interchangeable to selectively align with an airflow produced by the distribution fan.

20. The personal and portable essential oil diffusing system of claim 19, wherein the multi-compartment diffuser cartridge further includes:
an intake opening configured to align with the exhaust opening of the body portion and to extend the diffuser cavity therethrough; and
a top adaptor fitting aligned with and positioned opposite from the intake opening, wherein the top adaptor fitting is configured to couple with the intake opening of a breathing mask.

\* \* \* \* \*